(12) United States Patent
Hester, Jr.

(10) Patent No.: US 6,642,238 B2
(45) Date of Patent: Nov. 4, 2003

(54) OXAZOLIDINONE THIOAMIDES WITH PIPERAZINE AMIDE SUBSTITUENTS

(75) Inventor: Jackson B. Hester, Jr., Galesburg, MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/042,916

(22) Filed: Jan. 9, 2002

(65) Prior Publication Data

US 2002/0137754 A1 Sep. 26, 2002

Related U.S. Application Data

(63) Continuation-in-part of application No. 09/778,603, filed on Feb. 7, 2001, now abandoned.
(60) Provisional application No. 60/181,640, filed on Feb. 10, 2000.

(51) Int. Cl.[7] .................. A61K 31/496; C07D 413/10
(52) U.S. Cl. ................. 514/254.02; 514/254.03; 514/254.04; 514/254.1; 544/367; 544/369; 544/374; 544/379
(58) Field of Search .............. 544/369; 514/254.02

(56) References Cited

U.S. PATENT DOCUMENTS 6,362,189 B1 * 3/2002 Hester et al. .......... 514/254.01
6,465,456 B2 * 10/2002 Springer et al.

FOREIGN PATENT DOCUMENTS

| EP | 0 074 268 | 3/1983 |
|---|---|---|
| JP | 11-322729 | * 11/1999 |
| WO | WO93/23384 | 11/1993 |
| WO | WO95/07271 | 3/1995 |
| WO | WO95/14684 | 6/1995 |
| WO | 98/54161 | * 12/1998 |
| WO | WO99/12914 | 3/1999 |
| WO | WO00/73301 | 12/1999 |
| WO | WO99/64417 | 12/1999 |
| WO | WO00/21960 | 4/2000 |
| WO | WO00/27830 | 5/2000 |
| WO | 01/40222 | * 6/2001 |

OTHER PUBLICATIONS

Patent Abstracts of Japan vol. 2000, No. 02, Feb. 29, 2000 & JP 11 322729 A (Hokuriku Seiyaku CO LTD), Nov. 24, 1999 Cpds. 125,126 on p. 12; cpd. 48 on p. 85 abstract.

* cited by examiner

Primary Examiner—Emily Bernhardt
(74) Attorney, Agent, or Firm—Lucy X. Yang; Jonathan P. O'Brien

(57) ABSTRACT

The present invention provides a compound of formula I

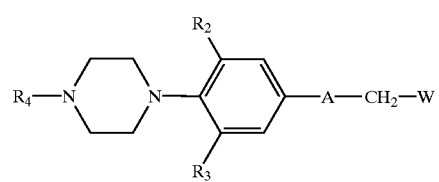

which have potent activities against gram-positive and gram-negative bacteria.

19 Claims, No Drawings

OXAZOLIDINONE THIOAMIDES WITH PIPERAZINE AMIDE SUBSTITUENTS

CROSS REFERENCE TO RELATED APPLICATIONS

This application is a continuation-in-part of U.S. Ser. No. 09/778,603 filed on Feb. 7, 2001 now abandoned, which claims the benefit of U.S. Ser. No 60/181,640, filed Feb. 10, 2000, under 35 USC 119(e)(i).

FIELD OF THE INVENTION

The present invention relates to novel oxazolidinone thioamides which have new piperazine amide substituents; and their preparations. These compounds have potent activities against gram positive and gram-negative bacteria.

BACKGROUND OF THE INVENTION

The oxazolidlinone antibacterial agents are a novel synthetic class of antimicrobials with potent activity against a number of human and veterinary pathogens, including gram-positive aerobic bacteria such as multiply-resistant staphylococci and streptococci, anaerobic organisms such as bacteroides and clostridia species, and acid-fast organisms such as Mycobacterium tuberculosis and Mycobacterium avium.

However, oxazolidinones generally do not demonstrate an activity at a useful level against aerobic gram-negative organisms. Thus, the use of these oxazolidinone antibacterial agents is limited to infectious states due to gram-positive bacteria. Accordingly, it is among the objects of the present invention to provide pharmaceutical compounds which have broader antibacterial activity including the activity against aerobic gram-negative organisms. We have now discovered that the oxazolidinone thioawnides of the present invention increase the spectrum of activity to include gram-negative organisms such as Haemophilus influenza and Moraxella catarrhalis.

INFORMATION DISCLOSURE

PCT International Publication WO 98/54161 discloses oxazolidinone antibacterial agents having a thiocarbonyl functionality.

PCT International Publication WO 93/23384 discloses oxazolidinones containing a substituted diazine moiety and their use as antimicrobials.

PCT International Publication WO 95/07271 discloses substituted oxazine and thiazine oxazolidinones and their use as antimicrobials.

PCT International Publication WO 99/12914 discloses antimicrobial thiourea derivatives.

SUMMARY OF THE INVENTION

The present invention provides a compound of formula I

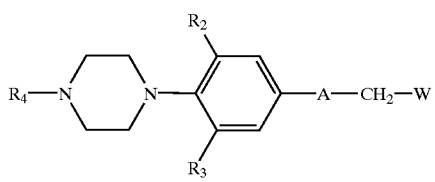

I or a pharmaceutically acceptable salt thereof wherein:

A is a structure i, ii, iii or iv:

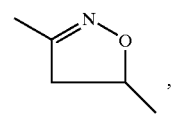

i

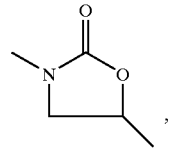

ii

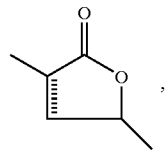

iii

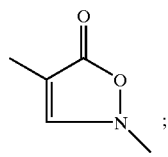

iv

W is NHC(=S)$R_1$, or —Y-het; provided that when A is a structure iv, W is not —Y-het;
Y is NH, O, or S;
$R^1$ is H, $NH_2$, $NHC_{1-4}$alkyl, $C_{1-4}$alkenyl, $OC_{1-4}$alkyl, or $SC_{1-4}$alkyl,
$(CH_2)_n$—$C_{3-6}$cycloalkyl, or $C_{1-4}$alkyl, optionally substituted with 1–3 F, 1–2 Cl or CN;
$R_2$ and $R_3$ are independently H, F, Cl or $C_{1-2}$alkyl;
$R_4$ is
  (a) —C(=O)—$CR_5R_6$—O—$R_7$,
  (b) —C(=O)—$CH_2S(O)_n$—$CH_3$,
  (c) —C(=O)—$CH_2$—S(=O)(=$NR_8$)$CH_3$,
  (d) —C(=S)—$R_9$,
  (e) —C(=O)—$CH_2$—O—$R_{10}$,
  (f) —C(=O)—$(CH_2)_m$—C(=O)—$CH_3$,
  (g) —C(=O)—$(CH_2OH)_2$—$CH_3$,
  (h) —C(=O)—$CH_2$—$CH_2$—$OR_{14}$, or
  (i) —CN;.
$R_5$ is H;
$R_6$ is phenyl, benzyl, $CH_2OH$ or $CH_2OCH_3$; or $R_5$ and $R_6$ taken together form $C_{3-5}$ cycloalkyl;
$R_7$ is H, $CH_3$ or $C_{1-4}$ alkanoyl;
$R_8$ is H, $C_{1-4}$ alkyl, $C_{1-4}$ alkanoyl, —C(=O)NH—$C_{1-4}$ alkyl or —$CO_2C_{1-4}$ alkyl;
$R_9$ is $C_{1-4}$ alkyl, $CH_2OR_{11}$, S—$C_{1-4}$ alkyl, $OC_{1-4}$ alkyl, or $NR_{12}R_{13}$;
$R_{10}$ is phenyl, —$CO_2$—$(CH_2)_2$—$OCH_3$, —P(=O)(OH)$_2$, —C(=O)—$NR_{12}R_{13}$, or —C(=O)—$(CH_2)_2$—$CO_2H$;
$R_{11}$ is H, phenyl, benzyl, $CH_3$ or C(=O)$CH_3$;
$R_{12}$ and $R_{13}$ are independently H or $C_{1-3}$ alkyl; or $R_{12}$ and $R_{13}$ taken together form a 5- or 6-membered saturated heterocycle, wherein said saturated heterocycle may further contain one or two additional hetero-atoms selected from a group consisting of 0, S(O)$_n$ or $NR_7$;
$R_{14}$ is H, $CH_3$ or benzyl;
het is a C-linked five-(5) membered heteroaryl ring having 1–4 heteroatoms selected from the group consisting of oxygen, sulfur, and nitrogen, or het is a C-linked six (6) membered heteroaryl ring having 1–3 nitrogen atoms; and n is 0, 1 or 2; and m is 0 or 1.

In another aspect, the present invention also provides:

a pharmaceutical composition comprising a compound of formula I or a pharmaceutically acceptable salt thereof, and a pharmaceutically acceptable carrier, a method for treating gram-positive microbial infections in humans or other warm-blooded animals by administering to the subject in need a therapeutically effective amount of a compound of formula I or a pharmaceutically acceptable salt thereof, and a method for treating gram-negative microbial infections in humans or other warm-blooded animals by administering to the subject in need a therapeutically effective amount of a compound of formula I or a pharmaceutically acceptable salt thereof.

The invention may also contain novel intermediates and processes that are useful for preparing compounds of formula I.

DETAILED DESCRIPTION OF THE INVENTION

The following definitions are used, unless otherwise described.

The term alkyl, alkenyl, etc. refer to both straight and branched groups, but reference to an individual radical such as "propyl" embraces only the straight chain radical, a branched chain isomer such as "isopropyl" being specifically referred to.

The carbon atom content of various hydrocarbon-containing moieties is indicated by a prefix designating the minimum and maximum number of carbon atoms in the moiety: i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The term "het" is a C-linked five-(5) membered heteroaryl ring having 1–4 heteroatoms selected from the group consisting of oxygen, sulfur, and nitrogen, or het is a C-linked six (6) membered heteroaryl ring having 1–3 nitrogen atoms.

Examples of "het" include pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone.

Mammal refers to human or animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

A specific value for A is structure ii as defined above.

A specific value for $R_1$ is $C_{1-4}$ alkyl.

A specific value for $R_1$ is ethyl.

A specific value for $R_2$ and $R_3$ are independently H or F.

A specific value for $R_2$ is H.

A specific value for $R_3$ is F.

A specific value for $R_4$ is C(=O)—CH(CH$_2$-phenyl)(OH).

A specific value for $R_4$ is C(=O)—CH$_2$—SO$_2$—CH$_3$.

A specific value for $R_4$ is C(=O)—CH(OH)(CH$_2$ OH).

A specific value for $R_4$ is C(=O)—C(=O)—CH$_3$.

A specific value for $R_4$ is C(=O)—CH(OH)(CH$_2$—O—CH$_3$).

A specific value for $R_4$ is C(=O)—CH$_2$CH$_2$—OH.

A specific value for $R_4$ is C(=O)—CH$_2$—O—CO$_2$—(CH$_2$)$_2$—OCH$_3$.

A specific value for $R_4$ is C(=S)—CH$_3$.

A specific value for $R_4$ is CN.

The preferred compounds of the present invention are those wherein structure i, ii, or iii has an optical configuration below:

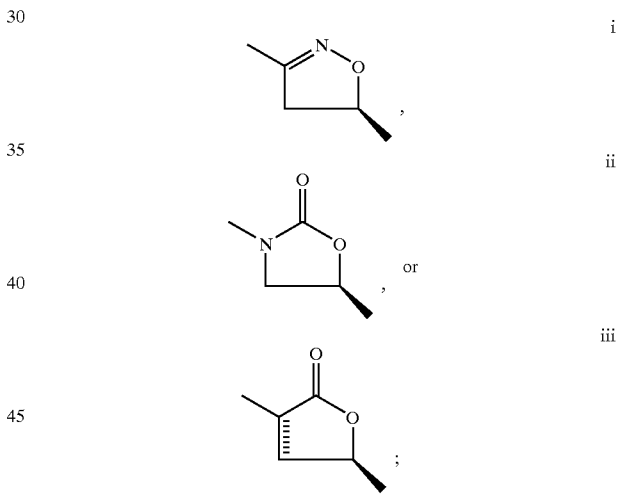

These absolute configurations are called (S)-configuration according to the Cahn-Ingold-Prelog nomenclature system. It will be appreciated by those skilled in the art that compounds of the present may have additional chiral centers and be isolated in optically active or racemic form. The present invention encompasses any racemic, optically-active, taulomeric, or stereoisomeric form, or mixture thereof, of a compound of the invention.

A more preferred compounds of the present invention is wherein A is structure ii that is optically pure enantiomer with the (S)-configuration at C5 of the oxazolidinone ring.

Examples of the present invention are:

(1) N{[(5S)-3-(3-fluoro-4-{4-[2-(methylsulfinyl)acetyl]-1-piperazinyl}phenyl)-2-oxo-1,3-oxazolidin-5-yl]methyl}propanethioamide, (2) N-{[(5S)-3-(3-fluoro-4-{4-[2-(methylsulfanyl)acetyl]-1-piperazinyl}phenyl)-2-oxo-1,3-oxazolidin-5-yl]methyl}propanethioamide, (3) N-{[(5S)-3-(3-fluoro-4-{4-[2-(methylsulfonyl)acetyl]-1-piperazinyl}phenyl]-2-oxo-1,3-oxazolidin-5-yl]methyl}propanethioamide, (4) N-({(5S)-3-[4-(4-ethanethiolyl-1-piperazinyl)-3-fluorophenyl]-2-oxo-1,3-oxazolidin-5-yl}methyl)propanethioamide, (5) N-({(5S)-3-[4-(4-cyano-1-piperazinyl)-3-fluorophenyl]-2-oxo-1,3-oxazolidin-5-yl}methyl)propanethioamide, (6) N-({(5S)-3-(3-fluoro-4-{4-[2-(methylaminocarbonyloxy) acetyl]-1-piperazinyl}phenyl)-2-oxo-1,3-oxazolidin-5-yl}methyl)propanethioamide, (7) N-({(5S)-3-(3-fluoro-4-{4-[2-[(2-methoxyethoxy)carbonyloxy]acetyl]-1-piperazinyl}phenyl)-2-oxo-1,3-oxazolidin-5-yl}methyl) propanethioamide, (8) N-[((5S)-3-{3-fluoro-4-[4-((2S)-2-hydroxy-3-methoxypropanoyl)-1-piperazinyl]phenyl}-2-oxo-1,3-oxazolidin-5-yl)methyl] propanethioamide, (9) N-[((5S)-3-{3-fluoro-4-[4-((2S)-2,3-dimethyoxypropanoyl)-1-piperazinyl]phenyl }-2-oxo-1,3-oxazolidin-5-yl)methyl]propanethioamide,

(10) N-[((5S)-3-{3-fluoro-4-[4-((2S)-3-hydroxy-2-methyoxypropanoyl)-1-piperazinyl]phenyl}-2-oxo-1,3-oxazolidin-5-yl)methyl] propanethioamide,

(11) N-({(5S)-3-[3-fluoro-4-(4-acetoacetyl-1-piperazinyl) phenyl]-2-oxo-1,3-oxazolidin-5-yl } methyl) propanethioamide,

(12) N-({(5S)-3-[3-fluoro-4-(4-pyruvoyl-1-piperazinyl) phenyl]-2-oxo-1,3-oxazolidin-5-yl } methyl) propanethioamide,

(13) N-({(5S)-3-[:3-fluoro-4-[4-(3-hydroxypropanoyl)-1-piperazinyl]phenyl]-2-oxo-1,3-oxazolidiin-5-yl } methyl] propanethioamide,

(14) N-{[(5S)-3-(3-fluoro-4-{4-[(1-hydroxycyclopropyl)carbonyl]-1-piperazinyl}phenyl)-2-oxo-1,3-oxazolidin-5-yl]methyl}propanethioamide,

(15) N-[((5S)-3-{3-fluoro-4-[4-(2-phenoxyacetyl)-1-piperazinyl]phenyl}-2-oxo-1,3-oxazolidin-5-yl)methyl] propanethioamide,

(16) N-({(5S)-3-[3-fluoro-4-[4-((2S)-2,3-dihydroxypropanoyl)-1-piperazinyl]phenyl]-2-oxo-1,3-oxazolidin-5-yl }methyl)propanethioamide,

(17) N-({(5S)-3-[3-fluoro-4-[4-((2R)-2,3-dihydroxypropanoyl)-1-piperazinyl]phenyl]-2-oxo-1,3-oxazolidin-5-yl }methyl)propanethioamide,

(18) N-{[(5S)-3-(3-fluoro-4-{4-[3-hydroxy-2-(hydroxymethyl)-2-methylpropanoyl]-1-piperazinyl}phenyl)-2-oxo-1,3-oxazolidin-5-yl]methyl}propanethioamide,

(19) N-[((5S)-3-{3-fluoro-4-[4-((2S)-2-hydroxy-3-phenylpropanoyl)-1-piperazinyl]phenyl }-2-oxo-1,3-oxazolidin-5-yl)methyl]propanethioamide,

(20) N-[((5S)-3-{3-fluoro-4-[4-((2R)-2-hydroxy-3-phenylpropanoyl)-1-piperazinyl]phenyl}-2-oxo-1,3-oxazolidin-5-yl) methyl]propanethioamide,

(21) N-[((5S)-3-{3-fluoro-4-[4-((2R)-2-hydroxy-2-phenylacetyl)-1-piperazinyl]phenyl }-2-oxo-1,3-oxazolidin-5-yl)methyl]propanethioamide, or

(22) N-[((5S)-3-{3-fluoro-4-[4-((2S)-2-acetoxy-2-phenylacetyl)-1-piperazinyl]phenyl}-2-oxo-1,3-oxazolidin-5-yl)methyl]propanethioamide.

Scheme I describes the preparation of compounds of the present invention. All of the starting materials are prepared by procedures described in these schemes or by procedures that would be well known to one of ordinary skill in organic chemistry. The variables used in Schemes I are as defined below or as in the claims. Optically pure material could be obtained either by one of a number of asymmetric syntheses or alternatively by resolution from a racemic mixture.

In step 1 of Scheme I, a suitably protected piperazine (II) is allowed to react with an activated carboxylic acid derivative to give compounds mi. In this reaction activated carboxylic acid derivatives can include acyl halides and acid anhydrides or mixed anhydrides which are allowed to react with II in the presence of a tertiary amine base such as triethylamine or pyridine in solvents such as methylene chloride, tetrahydrofuran (THF) or excess pyridine. Temperatures in the range of about 0° C. to about 24° C. are generally suitable for this reaction. Alternatively coupling agents which are well known for amide forming reactions can be used with appropriate carboxylic acids in step 1. Reagents such as dicyclohexylcarbodiimide (DCC) and 1-(3-dimethylaminopropyl)-3-ethylcarbodiimide hydrochloride (EDC) can be used with activating agents such as 1-hydroxybenzotriazole (HOBT) or 4-(dimethylamino) pyridine (DMAP) in this reaction. Solvents such as THF or dimethylformamide (DMF) and temperatures in the range of 0° C. to 24° C. are suitable. Compounds where $R_4$ is cyano are prepared by allowing compounds II to react with cyanogen bromide in solvents such as methanol. Sodium acetate is a suitable base for this reaction which can be carried out at temperatures in the range of 0° C. to 24° C. (See Example 5). Protecting groups (P) are chosen for their compatibility with other functional groups on the molecule. Benzyloxycarbonyl (Cbz) and tert-butoxycarbonyl (Boc) are generally suitable protecting groups for these compounds; however, it is sometimes necessary to employ other protecting groups. Example 1 illustrates the use of the phthalimide protecting group. In this example, the sulfoxide is sensitive to the acidic conditions required for Boc group removal. The phthalimide can be removed under non-acidic conditions with hydrazine hydrate or methylamine.

In step 2 of Scheme 1, the protecting group (P) is removed to give the corresponding amines (IV). It is convenient to remove the Boc group with hydrogen chloride in dioxane at 0° C. to 24° C.; however, other deprotection strategies can be employed. Deprotection of Cbz groups can generally be accomplished by hydrogenation with a palladium catalyst.

In step 3 of Scheme 1, the amines (IV) are converted to compounds of formula I. Thioamides are prepared by allowing compounds IV to react with dithioesters and a tertiary amine base such as triethylamine. In this reaction it is often convenient to employ an excess of the tertiary amine base with an amine salt prepared by Boc deprotection in step 2 without first isolating the free base. Solvents such as THF, methylene chloride or preferably methanol and temperatures in the range of about 24° C. to about 50° C. can be used for this reaction. Other thiocarbonyl compounds of formula I can be prepared according to the procedures disclosed in PCT International Publication WO 98/54161.

If desired $R_4$ of compounds I or III can be modified to give additional compounds of formula I. This is illustrated in Example 4 where the acetamide of 14 is allowed to react with Lawesson's reagent to give the thioamide 15, a compound of formula I. Other compounds of formula I, such as $R_4=C(S)-R_9$, can be prepared in a similar manner. In Example 1 it is shown in step 3 that the sulfide 3 can be oxidized to the sulfoxide 4 with sodium periodate in methanol-water. This intermediate 4 can subsequently be converted to a compound of formula I. The reaction of sulfoxides such as 4 (Example 1) with sodium azide in polyphosphoric acid at temperatures in the range of 40° C. to 70° C. gives sulfoximine intermediates that can also be converted to the corresponding compounds of formula I ($R_4$ is —C(=O)—CH$_2$—S(=O)(=NR$_8$)CH$_3$,). Other sulfoximine analogs can be obtained as described in U.S. Ser. No. 09/736,858, filed on Dec. 14, 2000. In Example 3 it is shown that the sulfide intermediate 8 can be oxidized to the sulfone 11 with osmium tetroxide and 4-methylmorpholine N-oxide in acetone-water. Intermediate 11 can subsequently be converted to compound 13, a compound of formula L. In Example 6 it is shown that the alcohol 19 will react with methylisocyanate and a cuprous chloride catalyst in DMF at 24° C. to give 20 which can be converted to 22, a compound of formula I. Other compounds of formula I (R$_4$=C(O)CH$_2$—O—R$_{10}$) can be prepared by methods similar to those described in Examples 6 and 7, using chemistry known in the art. And in Example 7 acylation of the alcohol 23 with 2-methoxyethyl chloroformate in pyridine gives 24, a compound of formula I. In a similar manner, using chemistry known in the art, other R$_4$ substituents of compounds I or III of Scheme I can be modified to give additional compounds of formula I.

desired concentration. Generally, the quantity of active component will range between 0.5% to 90% by weight of the composition.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 1.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively

SCHEME I

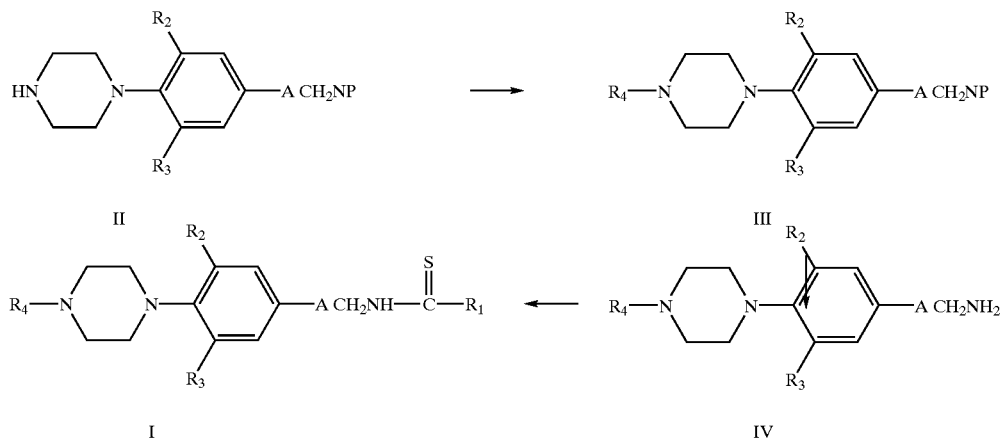

The pharmaceutical compositions of this invention may be prepared by combining the compounds of formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. As solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compounds of formula I according to this invention.

The quantity of active component, that is the compound of formula I according to this invention, in the pharmaceutical composition and unit dosage form thereof may be varied or adjusted widely depending upon the particular application, the potency of the particular compound and the increased during the course of treatment depending; on the particular situation. If desired, the daily dose may also be divided into multiple doses for administration, e.g., two to four times per day.

The compounds of formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds according to formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of formula I according to this invention are advantageously administered orally in solid and liquid dosage forms.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA. The activity of compounds of this invention against *Staphylococcus aureus, Staphylococcus epidermidis, Streptococcus pneumoniae, Streptococcus pyogens, Enterococcus faecalis, Moraxella catarrhalis* and *H. influenzae* is shown in Table 1.

TABLE 1

Antibacterial Activity Minimum Inhibitory Concentration (μg/mL)

| | SAUR 9213 MIC | SEPI 30593 MIC | EFAE 12712 MIC | SPNE 9912 MIC | SPYO 152 MIC | HINF 30063 MIC | EFAE 9217 MIC | MCAT 30607 MIC |
|---|---|---|---|---|---|---|---|---|
| EX 1 | 4 | 1 | 2 | .05 | 2 | 8 | 1 | 8 |
| EX 2 | 2 | 1 | 1 | <0.5 | 1 | >64 | 1 | 4 |
| EX 3 | 2 | 0.5 | 1 | 0.25 | 0.5 | 8 | 0.5 | 2 |
| EX 4 | 0.5 | 0.25 | 0.5 | 0.125 | 0.125 | 1 | 0.5 | 1 |
| EX 5 | 0.25 | 0.25 | 0.25 | 0.125 | 0.125 | 2 | 0.25 | 1 |
| EX 7 | 2 | 1 | 2 | 0.25 | 0.25 | 4 | 2 | 4 |
| EX 8 | 2 | 1 | 2 | 0.5 | 0.5 | 16 | 1 | 2 |
| EX 9 | 4 | 2 | 4 | 1 | 1 | 32 | 2 | 4 |
| EX 10 | 4 | 2 | 2 | 1 | 1 | 16 | 1 | 4 |
| EX 12 | 2 | 1 | 1 | 0.5 | 0.5 | 8 | 1 | 2 |
| EX 13 | 2 | 1 | 1 | 0.5 | 0.5 | 8 | 1 | 2 |
| EX 14 | 4 | 1 | 2 | 0.5 | 1 | 32 | 1 | 2 |
| EX 15 | 2 | 0.5 | 1 | 0.25 | 0.5 | 32 | 0.5 | 2 |
| EX 16 | 4 | 0.5 | 1 | 0.5 | 0.5 | 8 | 0.5 | 2 |
| EX 17 | 4 | 0.5 | 1 | 0.25 | 0.5 | 8 | 0.5 | 2 |
| EX 18 | 4 | 1 | 2 | 0.5 | 1 | 32 | 2 | 4 |
| EX 19 | 2 | 2 | 2 | <0.5 | 1 | >64 | 2 | 8 |
| EX 20 | 1 | 1 | 1 | <0.5 | 1 | 64 | 1 | 4 |
| EX 21 | 4 | 1 | 2 | 1 | 2 | 64 | 2 | 4 |
| EX 22 | 8 | 4 | 4 | 2 | 4 | >64 | 4 | 8 |

Example 1

Preparation of N{[(5S)-3-(3-fluoro-4-{4-[2-(methylsulfinyl)acetyl]-1-piperazinyl}phenyl)-2-oxo-1,3-oxazolidin-5-yl]methyl}propanethioamide (6) PNU-255889

Step 1

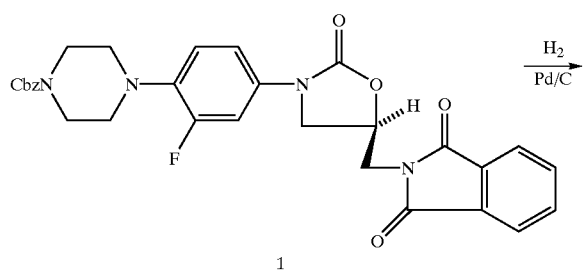

1

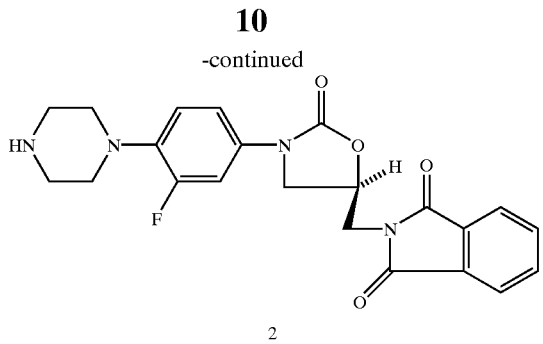

2

A mixture of 1 (may be prepared according to U.S. Pat. No. 5,547,950) (5.00 g, 8.95 mmol), EtOH (150 ml), THF (150 ml), concentrated hydrochloric acid (1.5 ml) and 10% palladium on carbon catalyst (2 g) is hydrogenated at an initial pressure of 32 p.s.i. for 18 hours. The mixture is filtered and the solid is washed with MeOH/CH₂Cl₂. Concentration of the combined filtrate gave a solid which is stirred for 18 hours with a mixture of saturated aqueous NaHCO₃ (100 ml) and EtOAc (100 ml), collected by filtration washed with water and dried. It is dissolved in 20% MeOH/CH₂Cl₂, dried (MgSO₄) and concentrated to give 1.94 g of compound 2.

Step 2

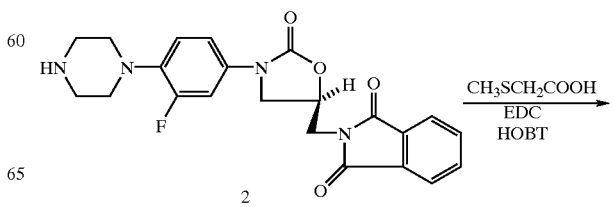

2

-continued

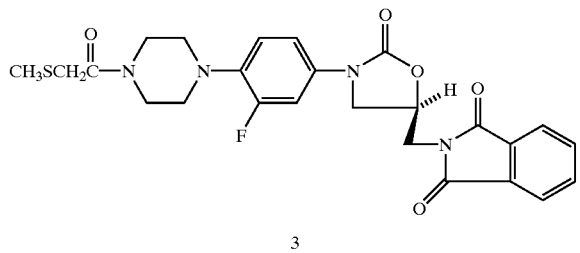

3

Step 3

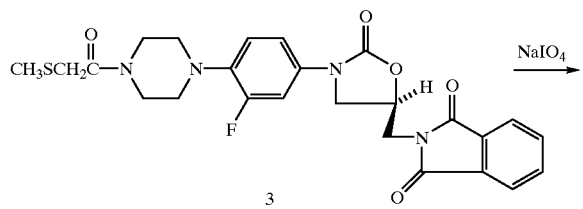

3

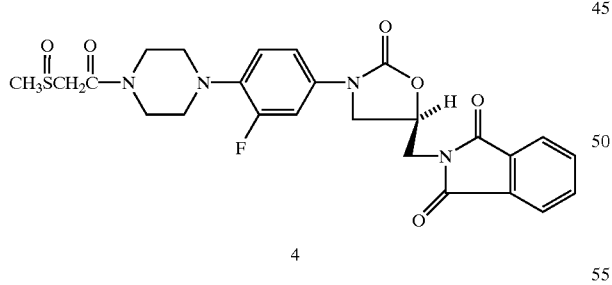

4

A stirred mixture of 2 (1.70 g, 4.01 mmol), 1-hydroxybenzotriazole hydrate (HOBT, 650 mg, 4.81 mmol), (methylthio)acetic acid (419 μL, 4.81 mmol) and DMF (38 ml) is cooled to 0° C. and treated with 1-(3-dimethylarinopropyl)-3-ethylcarbodiinide hydrochlroride (EDC, 1.54 g, 8.02 mmol). It is kept at 0° C. for two days and concentrated in vacuo at 50° C. The residue is mixed with water and extracted with EtOAc. The extract is dried (MgSO$_4$) and concentrated. Chromatography of the residue on silica gel with mixtures of MeOH/CH$_2$Cl$_2$ containing 1–2% MeOH gave 1.75 g of compound 3.

A stirred, ice cold mixture of 3 (1.70 g, 3.32 mmol) in MeOH (17 ml) and water (8.5 ml) is treated with sodium periodate (1.06 g, 4.98 mmol) and kept in the ice bath for 4 hours and at ambient temperature (24° C.) for 4 days. It is concentrated in vacuo, mixed with water and extracted with CH$_2$Cl$_2$. The extract is dried (MgSO$_4$) and concentrated. Chromatography of the residue on silica gel with 5% MeOH—CH$_2$Cl$_2$ gave 1.22 g of compound 4.

Step 4

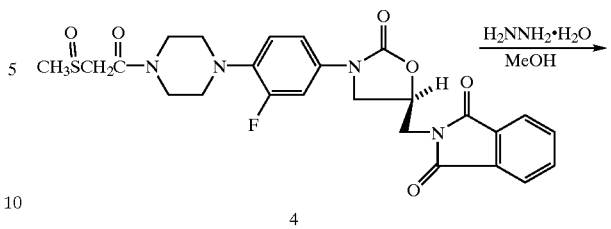

4

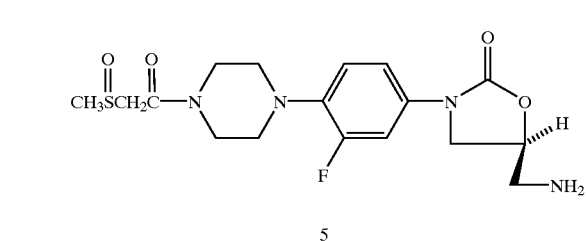

5

A stirred mixture of 4 (964 mg, 1.82 mmol), hydrazine hydrate (177 μL, 3.64 mmol) and MeOH (16 ml) is warmed at 80° C. for 6 hours and kept at ambient temperature for 4 days. It is concentrated in vacuo. Chromatography of the residue on silica gel with 10% MeOH-1% NH$_4$OH—CH$_2$Cl$_2$ gave 630 mg of compound 5.

Step 5

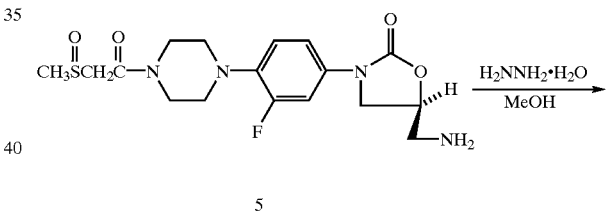

5

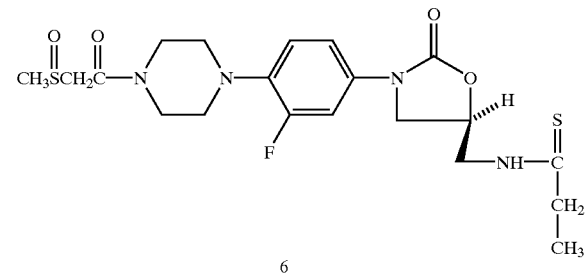

6

A stirred mixture of 5 (326 mg, 0.815 mmol), triethylamine (0.91 mL, 6.55 mmol), and methyl clithiopropionate (393 mg, 3.27 mmol) in CH$_2$Cl$_2$ (8.0 ml) and THF (8 ml) is kept at ambient temperature (24° C.) for 18 hours, mixed with water and extracted with CH$_2$Cl$_2$. The extract is dried (MgSO$_4$) and concentrated. Chromatography of the residue on silica gel with mixtures of MeOH/CH$_2$Cl$_2$ containing 2.5–5% MeOH gave the product which is recrystallized from MeOH to give 257 mg of compound 6. Anal. calcd for C$_{10}$H$_{27}$FN$_4$O$_4$S$_2$: C, 51.05; H, 5.78; N, 11.91. Found: C, 50.82; H, 5.85; N, 11.80.

Example 2

Preparation of N-{[(5S)-3-(3-fluoro-4-{4-[2-(methylsulfanyl)acetyl]-1-piperazinyl}phenyl)-2-oxo-1,3-oxazolidin-5-yl]methyl}propanethioamide (10) (PNU-247827)

Step 1

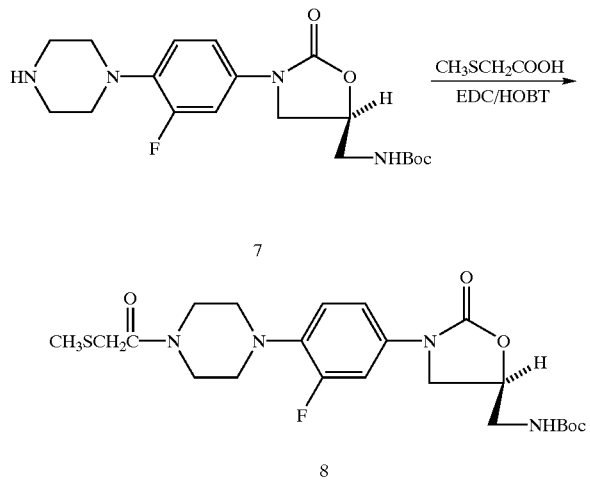

A stirred, ice cold, solution of 7 (may be prepared according to PCT International Publication WO 98/54161) (3.00 g, 7.61 mmol), HOBT (1.13 g, 2.79 mmol) and methylthioacetic acid (0.66 mL, 2.54 mmol) in DMF (69 ml) are treated with EDC (3.21 g, 5.58 mmol) and allowed to warm slowly to ambient temperature (24° C.) during about 18 hours. It is concentrated in vacuo at 50° C. and the residue is mixed with water and extracted with EtOAc. The extract is washed with water and brine, dried (MgSO$_4$) and concentrated. Crystallization of the residue from MeOH/EtOAc/heptame gave 2.36 g of compound 8.

Step 2

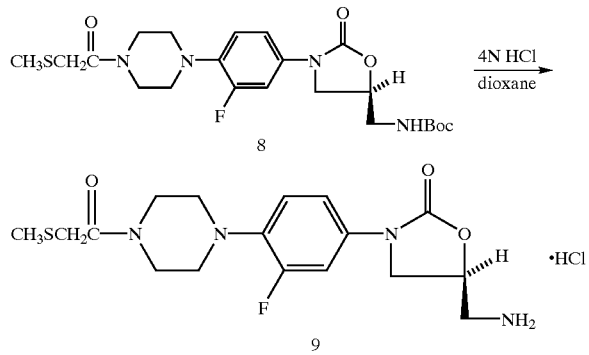

A sample of 8 (1.00 g, 2.07 mmol) is cooled in an ice bath, treated with 4N HCl in dioxane (10 ml) and stirred in the bath for 1.5 hours and at ambient temperature (24° C.) for 1 hour. The mixture is concentrated and the residue is mixed with three portions of CH$_2$Cl$_2$ with concentration after each addition to give 9.

Step 3

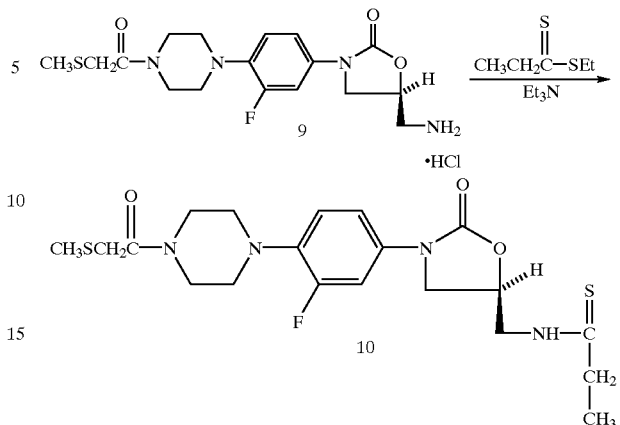

A stirred mixture of compound 9 (578 mg, 1.38 mmol), triethylamine (1.5 mL, 11.0 mmol), ethyl dithiopropionate (0.76 mL, 5.52 mmol), CH$_2$Cl$_2$ (15.5 ml) and THF (15.5 ml) is kept at ambient temperature (24° C.) for 18 hours and concentrated in vacuo. The residue is stirred with a mixture of water (30 ml) and 10% EtOAc-heptane (30 ml) for 2 hours and the solid is collected by filtration, washed with water, dried and crystallized from EtOAc-MeOH-heptane. The resulting solid is chromatographed on silica gel with 2% MeOH—CH$_2$Cl$_2$ and the product is crystallized from MeOH/EtOAc to give 465 mg of compound 10: MS (EI) m/z 454 (M+). Anal. Calcd for C$_{20}$H$_{27}$FN$_4$O$_3$S$_2$: C, 52.84; H, 5.99; N, 12.32. Found: C, 52.83; H, 6.02; N, 12.23.

Example 3

Preparation of N-{ [(5S)-3-(3-fluoro-4-{4-[2-(methylsulfonyl)acetyl]-1-5 piperazinyl}phenyl]-2-oxo-1,3-oxazolidin-5-yl]methyl }propanethioamide (13) (PNU-248337)

Step 1

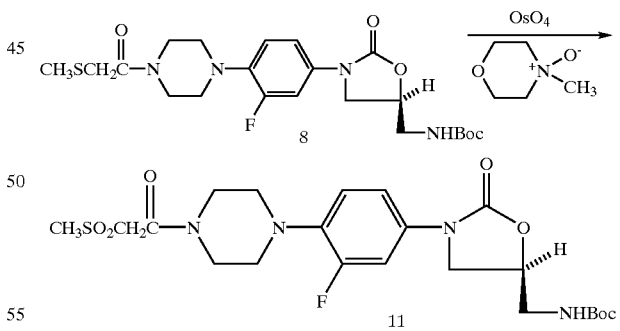

A stirred mixture of compound 8 (100 mg, 0.207 mmol), 4-methylmorpholine, N-oxide (73 mg, 0.621 mmol), acetone (1.5 ml) and water (0.5 ml) is treated with a 2.5% solution of osmium tetroxide in 2-methyl-2-propanol (17 μL) and kept at ambient temperature (24° C.) for 18 hours. It is then treated with 10% aqueous NaHSO$_3$ (60 ml) and extracted with CH$_2$Cl$_2$. The extracts are washed with 10% NaHSO$_3$, dried (MgSO$_4$) and concentrated. Crystallization of the residue from EtOAc-heptane gave 96 mg of 11: MS (EI) m/z 514 (M+).

Step 2

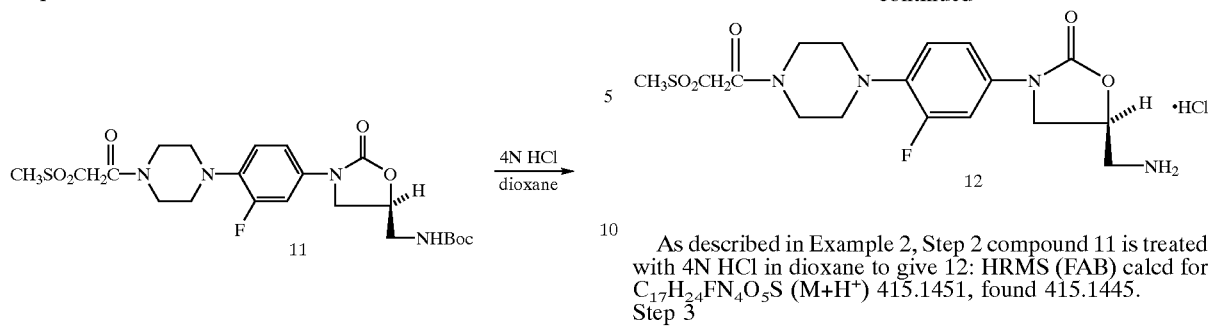

As described in Example 2, Step 2 compound 11 is treated with 4N HCl in dioxane to give 12: HRMS (FAB) calcd for $C_{17}H_{24}FN_4O_5S$ (M+H$^+$) 415.1451, found 415.1445.

Step 3

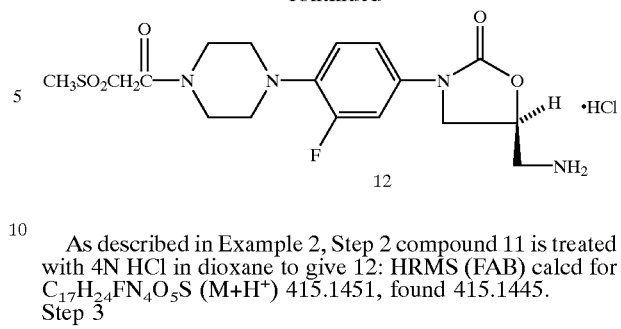

As described in Example 2, Step 3 compound 12 is allowed to react with ethyl dithiopropionate and triethylamine to give 13 which is purified by chromatography on silica gel with 1% MeOH—$CH_2Cl_2$ and crystallization from MeOH—EtOAc: MS (EI) m/z 486 (M$^+$); HRMS (FAB) calcd for $C_{20}H_{28}FN_4O_5S_2$ (M+H$^+$) 487.1485, found 487.1494. Anal. Calcd for $C_{20}H_{27}FN_4O_5S_2$: C, 49.37; H, 5.59; N, 11.51. Found: C, 49.25; H, 5.63; N, 11.47.

Example 4

Preparation of N-({(5S)-3-[4-(4-ethanethiolyl-1-piperazinyl)-3-fluorophenyl]2-oxo-1,3-oxazolidin-5-yl}methyl)propanethioamide (15) (PNU-276575).

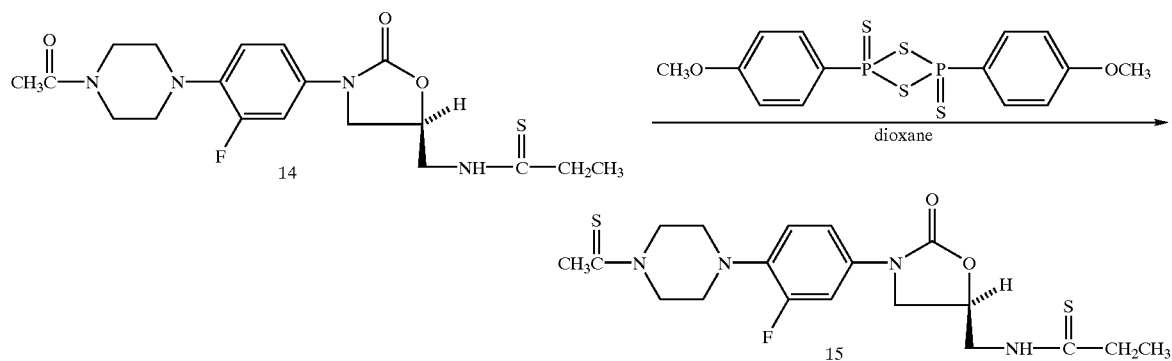

A stirred mixture of 14 ((S)-N-[[3-[3-fluoro-4-(4-acetyl-1-piperazinyl)phenyl]-2-oxo-5-oxazolidinyl]methyl] propanethioamide (may be prepared according to the procedure disclosed in PCT International Publication WO 98/54161) (0.53 g, 1.3 mmol), Lawesson's Reagent (0.53 g)

and dioxane (27 ml) is refluxed, under nitrogen for 90 min, cooled and concentrated in vacuo. Chromatography of the residue on silica gel with 2% MeOH—CH$_2$Cl$_2$ gave the product which is decolorized with activated carbon and crystallized from acetonitrile to give 0.303 g of 15: mp 209–210° C. Anal. Calcd for C$_{19}$H$_{25}$FN$_4$O$_2$S$_2$: C, 53.75; H, 5.93; N, 13.20. Found: C, 53.69; H, 6.00; N, 13.25.

Example 5

Preparation of N-({(5S)-3-[4-(4-cyano-1-piperazinyl)-3-fluorophenyl]-2-oxo-1,3-oxazolidin-5-yl}methyl)propanethioamide (18) (PNU-278605)

Step 1

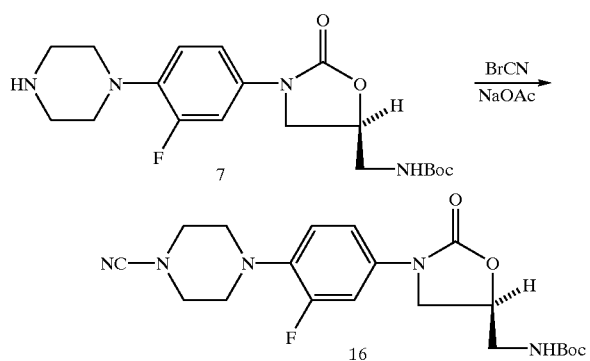

A stirred, ice cold mixture of 7 (0.488 g, 1.24 mmol) and sodium acetate (0.55 g, 6.7 mmol) in MeOH (40 ml) is treated during 1 minute, with a MeOH (10 ml) solution of 5M cyanogen bromide in CH$_2$Cl$_2$ (0.35 ml, 1.48 mmol) and kept in the ice bath for 2 hours. It is then concentrated in vacuo and the residue is mixed with dilute NaHCO$_3$ and extracted with CH$_2$Cl$_2$. The extract is washed with water, dried (Na$_2$SO$_4$) and concentrated. Chromatography of the residue on silica gel with 2% MeOH—CH$_2$Cl$_2$ gave 0.42 g of 16: MS(ES) m/z 420 (M+H$^+$).

Step 2

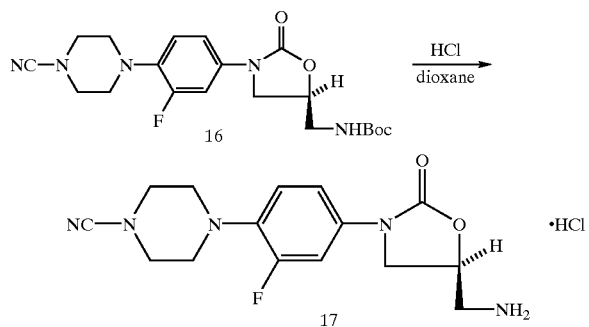

A stirred ice cold suspension of 16 (0.42 g, 1.0 mmol) in dioxane (10 ml), under nitrogen is treated dropwise with ice cold 4N HCl in dioxane (10 ml), kept in the ice bath for 2 hours and concentrated in vacuo. The residue is dried in vacuo for 18 hours to give 17: MS(ES) m/z 320 (M+H$^+$).

Step 3

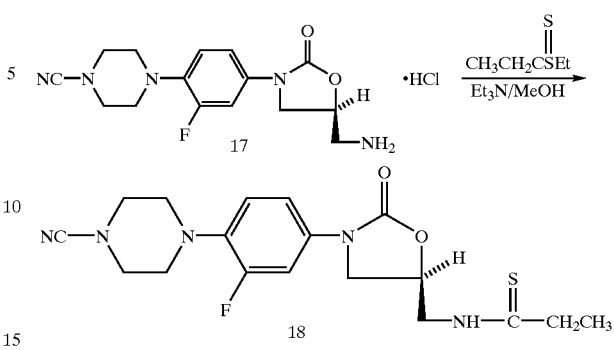

A stirred mixture of 17 (0.25 g, 0.64 mmol), and triethylamine (0.178 ml) in MeOH (5 ml), under nitrogen is warmed to 50° C. during 30 minutes, kept at 50° C. for 30 minutes and cooled in an ice bath. The solid is collected by filtration and crystallized from EtOH to give 18: mp 182–184° C.; HRMS (FAB) calcd for C$_{18}$H$_{23}$FN$_5$O$_2$S (M+H$^+$) 392.1556, found 392.1550.

Example 6

Preparation of N-({(5S)-3-(3-fluoro-4-{4-[2-(methylaminocarbonyloxy) acetyl]-1-piperazinyl}phenyl)-2-oxo-1,3-oxazolidin-5-yl}methyl)propanethioamide (22) (PNU-281328)

Step 1

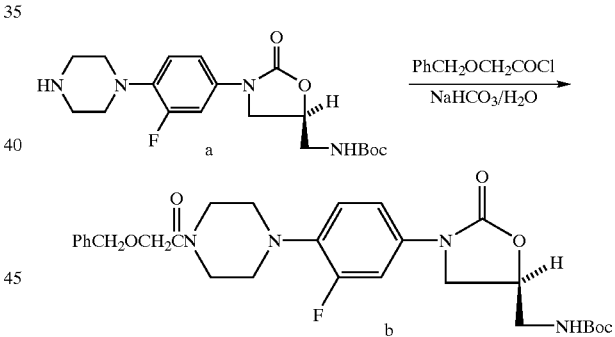

A stirred, ice cold mixture of a (PCT International Publication WO 98/54161) (20.0 g, 50.7 mmol), acetone (1500 mL) and saturated aqueous sodium bicarbonate (500 ml) is treated, during 20 min, with a solution of benzyloxyacetyl chloride (9.5 ml, 60.8 mmol) in acetone (150 ml). The mixture is allowed to warm slowly to ambient temperature (24° C.) and stand for 18 hours. It is extracted with Et$_2$O and the extract is washed with water and brine, dried (MgSO$_4$), and concentrated to give 25.4 g of the product b.

Step 2

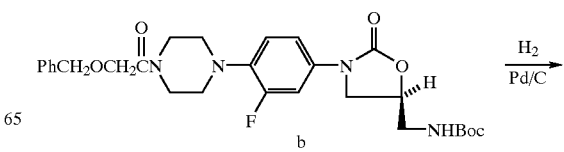

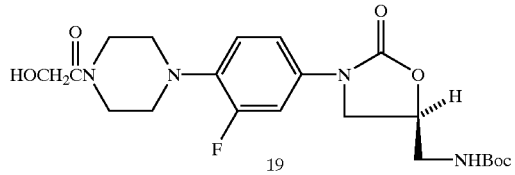

A mixture of 2 (25.0 g, 46.1 mmol), MeOH (1700 ml) and 10% palladium—on —carbon catalyst (6.25 g) is hydrogenated at an initial pressure of 35 p.s.i. for 4 days. Additional catalyst (6.25 g) is added and the hydrogenation is continued for 1 day. The mixture is filtered and the filtrate is concentrated. Chromatography of the residue on silica gel with 2.5% MeOH—$CH_2Cl_2$ gave the product which is crystallized from acetone—$CH_2Cl_2$ to give 13.7 g of 3.

Step 3

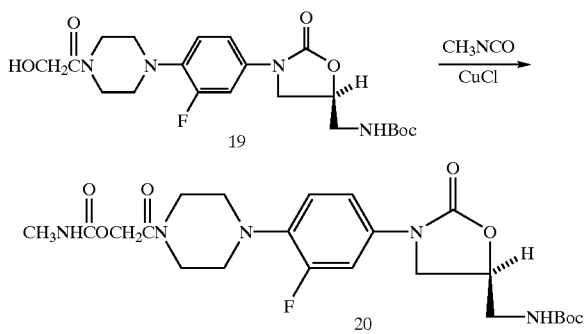

A stirred mixture of 19 and cuprous chloride (0.075 g) in DMF (4 ml) is treated with methyl isocyanate (0.081 ml), kept at ambient temperature (24° C.) for 60 minutes and concentrated in vacuo. The residue is mixed with water and $Et_2O$ to give a solid which is collected by filtration and chromatographed on silica gel with 2.5% MeOH—$CH_2Cl_2$ to give 0.28 g of 20.

Step 4

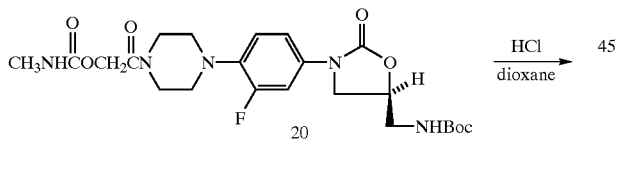

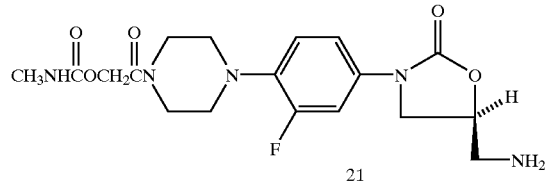

An ice cold, stirred mixture of 20 (0.37 g, 0.726 mmol) in dioxane (10 ml), under nitrogen is treated, drop-wise with ice cold 4N hydrogen chloride in dioxane (8 ml). The mixture is kept in the ice bath for 1 hour 15 minutes and at ambient temperature (24° C.) for 1 hour. It is diluted with additional dioxane (10 ml), kept at ambient temperature for 30 minutes, at 0° C. for 18 hours and at ambient temperature for 6 hours. It is concentrated in vacuo to give 21: MS(ES) m/z 410 (M+H$^+$).

Step 5

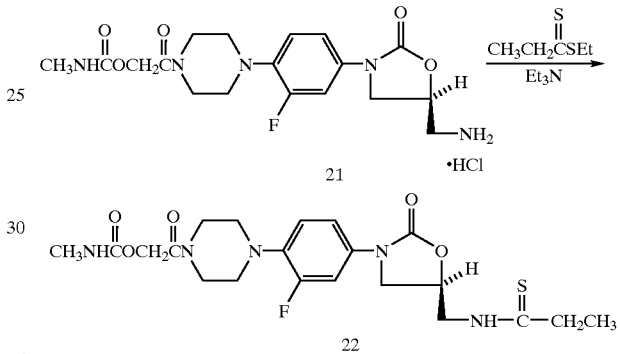

A stirred mixture of 21 (0.20 g, 0.416 mnmol), ethyl dithiopropionate (0.17 ml) and triethylamine (0.5 ml) in $CH_2Cl_2$ (20 ml) and MeOH (5 ml) is kept, under nitrogen at ambient temperature (24° C.) for 21 hours and concentrated under a stream of nitrogen. Chromatography of the residue on silica gel with 2% MeOH—$CH_2Cl_2$ gave 22: HRMS (FAB) calcd for $C_{21}H_{29}FN_5O_5S$ (M+H$^+$) 482.1873, found 482.1873.

Example 7

Preparation of N-({(5S)-3-(3-fuoro-4-{4-[2-[(2-methoxyethoxy) carbonyloxy]acetyl]-1-piperazinyl}phenyl)-2-oxo-1,3-oxazolidin-5-yl}methyl) propanethioamide (24) (PNU-276528)

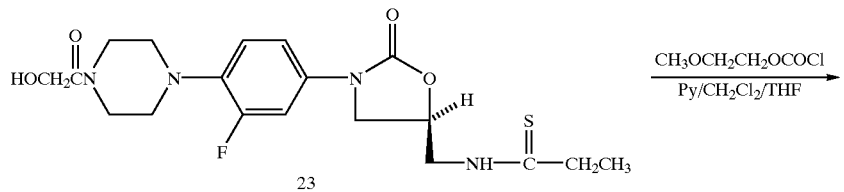

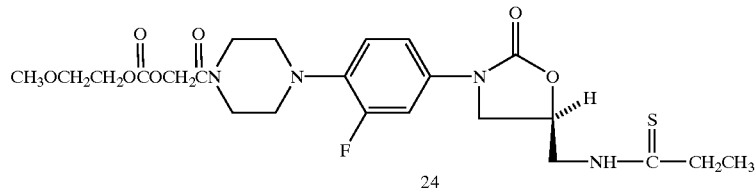

A stirred, ice cold mixture of 23 (may be prepared according to the procedure disclosed in PCT International Publication WO 98/54161) (0.212 g, 0.496 mmol) and pyridine (0.2 ml, 2.5 mmol) in CH$_2$Cl$_2$ (5 ml) and THF (5 ml) is treated, dropwise with 2-methoxyethyl chloroformate (0.069 g, 0.5 mmol) and kept in the ice bath for 1 hour and at ambient temperature (24° C.) for 2 hours. Additional 2-methoxyethyl chloroformate (0.07 ml) is added; the mixture is kept at ambient temperature for 3 hours and again treated with additional 2-methoxyethyl chloroformate (0.1 ml). This mixture is kept at ambient temperature for 18 hours. It is mixed with saturated aqueous NaHCO$_3$ and extracted with CH$_2$Cl$_2$. The extract is washed with water and brine, dried (Na$_2$SO$_4$) and concentrated. Chromatography of the residue on silica gel with 2.5% MeOH—CH$_2$Cl$_2$ gave the product which is crystallized from EtOAc to give 0.185 g of 24: mp 150–151° C. Anal. Calcd for C$_{23}$H$_{31}$FN$_4$O$_7$S: C, 52.46; H, 5.93; N, 10.64. Found: C, 52.45, H, 6.05; N, 10.61.

Example 8

Preparation of N-[((5S)-3-{3-fluoro-4-[4-((2S)-2-hydroxy-3-methoxypropanoyl)-1-piperazinyl]phenyl}-2-oxo-1,3-oxazolidin-5-yl)methyl] propanethioamide (33) (PNU-272200).

Step 1

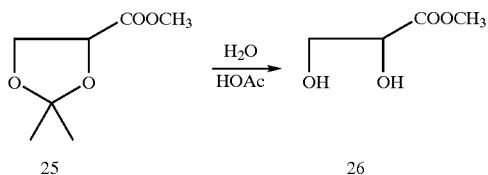

A stirred solution of methyl (S)-(−)-2,2-dimethyl-1,3-dioxolane-4-carboxylate (25) (5.0 g, 0.031 mol) in acetic acid (10 ml) and water (2.5 mil) is kept at ambient temperature for 72 hours and concentrated in vacuo to give (S)-26.

Step 2

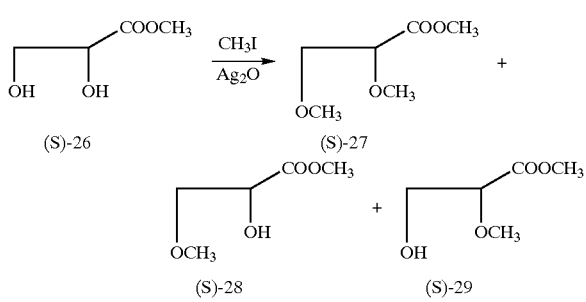

A stirred mixture of (S)-26 (1.0 g) from Step 1 and methyl iodide (20 ml), under nitrogen is treated with silver oxide (1.3 g) and 3A molecular sieves (2 g) and warmed at 43° C. for 90 minutes. It is cooled and filtered. The filtrate is concentrated and the residue is chromatographed on silica gel with mixtures of MeOH—CH$_2$Cl$_2$ containing 2–4% MeOH. The products eluted from the column are (S)-27 (0.15 g), (S)-28 (0.08 g), and (S)-29 (0.28 g).

Step 3

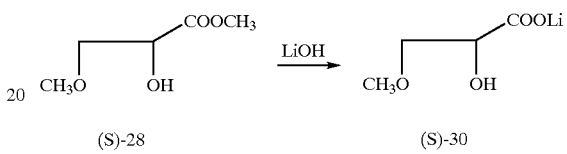

A stirred mixture of (S)-28 (0.08 g, 0.6 mmol) and MeOH (3.0 ml) under nitrogen, is treated with 1M lithium hydroxide (0.57 ml) and kept at ambient temperature (24° C.) ]or 3 hours and under a stream of nitrogen for 18 hours. It is then concentrated in vacuo to give (S)-30.

Step 4

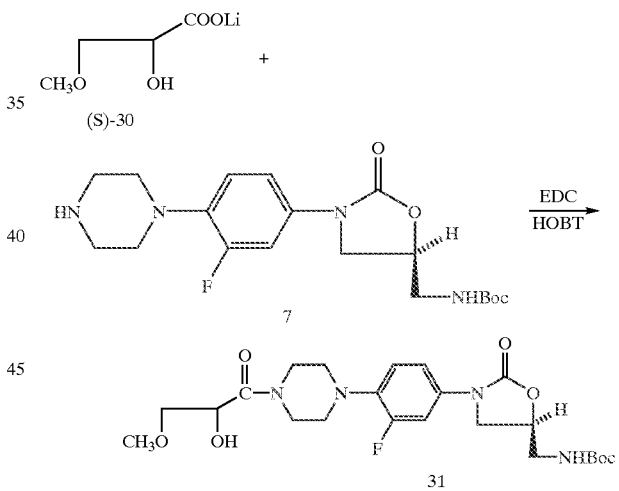

A stirred mixture of 7 (0.237 g, 0.601 mmol), the product ((S)-30) from Step 3, HOBT 0.095 g (0.703 mmol) and DMF (4 ml), under nitrogen, is treated with EDC (0.26 g, 1.36 mmol), kept at ambient temperature (24° C.) for 2.5 hours and concentrated in vacuo. The residue is chromatographed on silica gel with 2.5% MeOH—CH$_2$Cl$_2$ to give 0.18 g of 31: MS(ES) m/z 497 (M+H$^+$).

Step 5

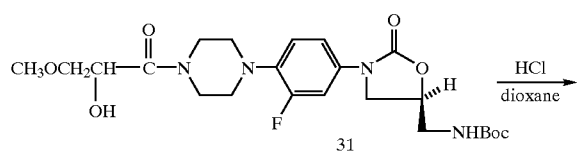

-continued

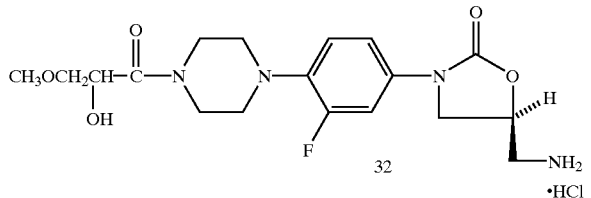

An ice cold stirred mixture of 31 (0.17 g, 0.342 mmol) in dioxane (10 ml), under nitrogen, is treated, dropwise during 3 minutes with cold 4N HCl in dioxane (10 ml) and kept in the ice bath for 50 minutes, at ambient temperature (24° C.) for 90 minutes and at 0° C. for 18 hours. It is then concentrated in vacuo to give 32: MS(ES) m/z 397 (M+H$^+$).
Step 6

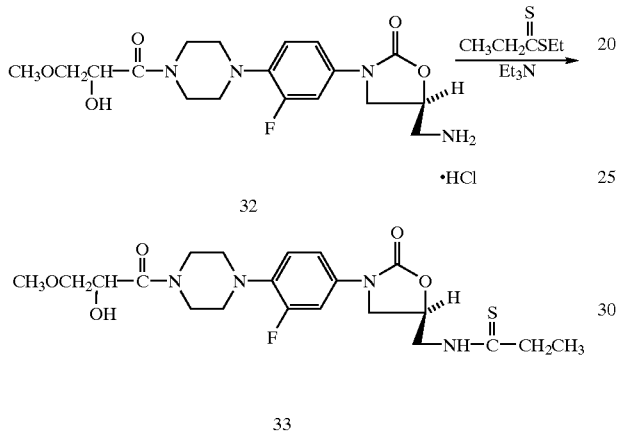

A stirred mixture of 32 from Step 5, triethylamine (0.5 ml, 3.5 mmol), CH$_2$Cl$_2$ (10 ml and THF (7 nil), under nitrogen is treated, dropwise with ethyl dithiopropionate (0.22 ml, 1.71 mmol) and kept at ambient temperature (24° C.) for 72 hours. Additional ethyl dithiopropionate (0.22 ml) is added and the mixture is kept at ambient temperature for 24 hours and concentrated. The residue which still contain 32 is mixed with CH$_2$Cl$_2$ (10 ml), THF (7 ml), triethylamine (0.75 ml) and ethyl dithiopropionate (0.35 ml), kept at ambient temperature for 24 hours and concentrated. Chromatography of the residue on silica gel with 2.5% MeOH—CH$_2$Cl$_2$ gave 0.0457 g of 33: mp 190–191° C. (dec). Anal. Calcd for C$_{21}$H$_{29}$FN$_4$O$_5$S: C, 53.83; H, 6.24; N, 11.96. Found: C, 53.59; H, 6.35; N, 11.83.

Example 9

Preparation of N-[((5S)-3-{3-fluoro-4-[4-((2S)-2,3-dimethyoxypropanoyl)-1-piperazinyl]phenyl}-2-oxo-1,3-oxazolidin-5-yl)methyl]propanethioamide (34) (PNU-272199)

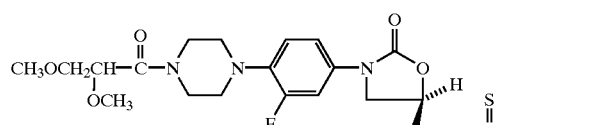

As described in Example 8 the ester ((S)-27, prepared in Step 2) is hydrolyzed with lithium hydroxide and coupled with 7. The resulting amide is deprotected and allowed to react with ethyl dithiopropionate and triethylamine. The product is purified by silica gel chromatography with 2.5% MeOH—CH$_2$Cl$_2$ and crystallized form EtOAc-hexane to give 34: mp 140–142° C. (dec). Anal. calcd for C$_{22}$H$_{31}$FN$_4$O$_5$S: C, 54.76; H, 6.47; N, 11.61. Found: C, 54.53; H, 6.54; N, 11.50.

Example 10

Preparation of N-[((5S)-3-{3-fluoro-4-[4-((2S)-3-hydroxy-2-methyoxypropanoyl)-1-piperazinyl]phenyl}-2-oxo-1,3-oxazolidin-5-yl)methyl]propanethioamide (35) (PNU-272198)

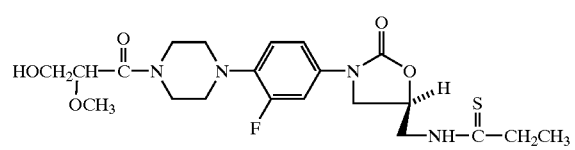

As described in Example 8 the ester ((S)-29, prepared in Step 2) is hydrolyzed with lithium hydroxide and coupled with 7. The resulting amide is deprotected and condensed with ethyl dithiopropionate. The product is purified by silica gel chromatography with 2.5% MeOH—CH$_2$Cl$_2$ to give 35. Anal. calcd for C$_{21}$H$_{29}$FN$_4$O$_5$S: C, 53.83; H, 6.24; N, 11.96. Found: C, 53.71; H, 6.32; N, 11.85.

Example 11

Preparation of N-({(5S)-3-[3-fluoro-4-(4-acetoacetyl-1-piperazinyl)phenyl]-2-oxo-1,3-oxazolidin-5-yl}methyl)propanethioamide (36)

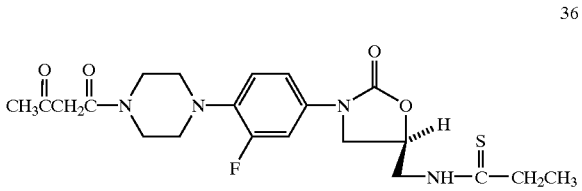

As described in Example 8 (Steps 4–6) the lithium salt of acetylacetic acid is coupled with 7 and the resulting amide is deprotected and allowed to react with ethyl dithiopropionate and triethylamine. The product is purified by silica gel chromatography to give 36: MS(ES) m/z 451 (M+H$^+$), 473 (M+Na$^+$).

Example 12

Preparation of N-({(5S)-3-[3-fluoro-4-(4-pyruvoyl-1-piperazinyl) phenyl]-2-oxo-1,3-oxazolidin-5-yl}methyl)propanethioamide (37) PNU-264886

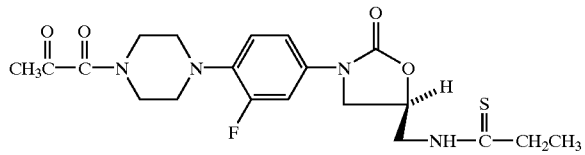

37

As described in Example 8 (Steps 4–6) pyruvic acid is coupled with 7 and the resulting amide is deprotected and allowed to react with ethyl dithiopropionate and triethylamine. The product is purified by silica gel chromatography with 2% MeOH—CH$_2$Cl$_2$ and crystallized from EtOAc-hexane to give 37: mp 173–175° C. (dec); MS(ES) m/z 437 (M+H$^+$), 459 (M+Na$^+$). Anal. calcd for C$_{20}$H$_{25}$FN$_4$O$_4$S·0.1 EtOAc; C, 54.97; H, 5.84; N, 12.57. Found: C, 55.05; H, 6.15; N, 12.12.

Example 13

Preparation of N-({(5S)-3-[3-fluoro-4-[4-(3-hydroxypropanoyl)-1-piperazinyl]phenyl]-2-oxo-1,3-oxazolidin-5-yl}methyl]propanethioamide (43) (PNU-272690)

Step 1

38

An ice cold, stirred solution of benzyl alcohol (4.0 mL, 0.0386 mol) in THF (20 mL), under nitrogen is treated, portionwise during 40 minutes with a 60% oil dispersion of sodium hydride (1.6 g, 0.04 mol), kept in the ice bath for 20 minutes and treated during 5 minutes with a solution of 3-chloropropionyl chloride (1.50 mL, 0.0157 mol) in THF (3 mL). The mixture is warmed slowly to ambient temperature (24° C.), kept for 23 hours, mixed with saturated ammonium chloride (15 mL) and ice water and extracted with EtOAc. The extract is washed with water and brine, dried (Na$_2$SO$_4$) and concentrated to give 38: MS(ES) m/z 293 (M+Na$^+$).

Step 2

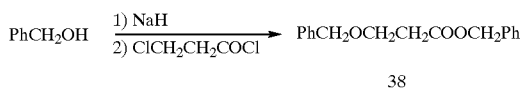

An ice cold, stirred solution of 38 from Step 1 in MeOH (50 ML), under nitrogen, is treated with potassium hydroxide (0.94 g, 0.0168 mol) and kept in the ice bath for 10 minutes, at ambient temperature for 1 hour and at –20° C. for 18 hours. It is treated with additional potassium hydroxide (0.98 g), kept at ambient temperature 10 for 8.5 hours and at –20° C. for 18 hours and concentrated in vacuo. The residue is mixed with ice water, cooled in an ice bath and treated with 2N HCl to pH 3. It is extracted with EtOAc. The extract is washed with 2N NaOH and water and the wash is reacidified with 2N HCl and extracted with EtOAc. The extract is concentrated to give 1.48 g of 39: MVIS(ES) m/z 181 (M+H$^+$), 203 (M+Na$^+$).

Step 3

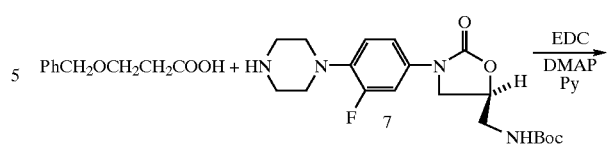

39

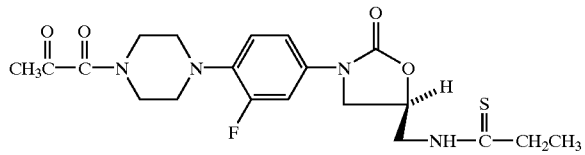

40

A stirred mixture of 7 (0.5 g, 1.26 mmol) and pyridine (6 mL), under nitrogen, is treated with 4-(dimethylamino)pyridine (DMAP, 8 mg), EDC (0.243 g, 1.26 mmol) and a solution of 39 (0.228 g, 1.26 mmol) in CH$_2$Cl$_2$ (2 mL) and kept at ambient temperature (24° C.) for 2 hours 20 minutes. It is concentrated in vacuo and the residue is mixed with CH$_2$Cl$_2$, washed with saturated NaHCO$_3$, water and brine, dried (Na$_2$SO$_4$) and concentrated. Chromatography of the residue on silica gel with 2.5% MeOH—CH$_2$Cl$_2$ gave 0.43 g of 40: MS (ES) m/z 557 (M+H$^+$), 579 (M+Na$^+$).

Step 4

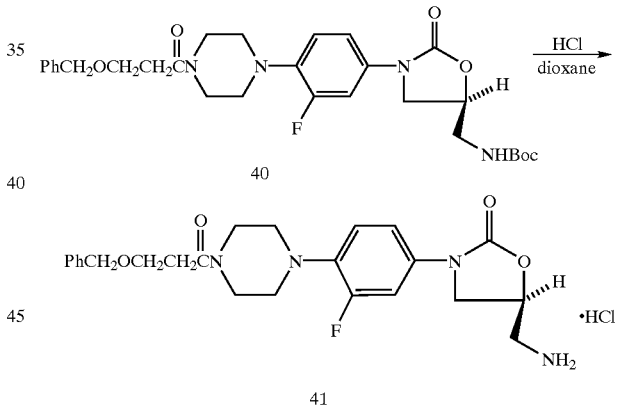

A stirred, ice cold solution of 40 (0.43 g, 0.772 mmol) in dioxane (12 mL), under nitrogen is treated with 4N hydrogen chloride in dioxane (10 mL), dropwise during 3 minutes. It is warmed to ambient temperature (24° C.) during 90 minutes, kept for 3 hours 30 minutes and concentrated to give 0.43 g of 41.

Step 5

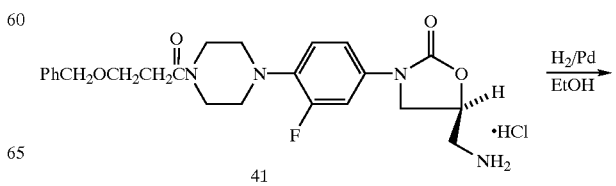

41

-continued

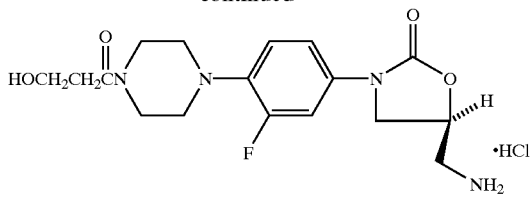

42

A mixture of 41 (0.21 g), 10% palladium on carbon catalyst (0.17 g) and EtOH (50 mL) is hydrogenated at an initial pressure of 44 p.s.i. for 90 minutes, treated with additional catalyst (0.1 g) and hydrogenated at an initial pressure of 40 p.s.i. for 22 hours. It is filtered and the solid is washed with MeOH. The filtrates are concentrated and the residue is chromatographed on silica gel with mixtures of MeOH—$NH_4OH$—$CH_2Cl_2$ that contained 5–7.5% MeOH and 0.25–0.5% $NH_4OH$ to give 0.07 g of 42: MS(ES;) m/z 367 (M+H$^+$).

Step 6

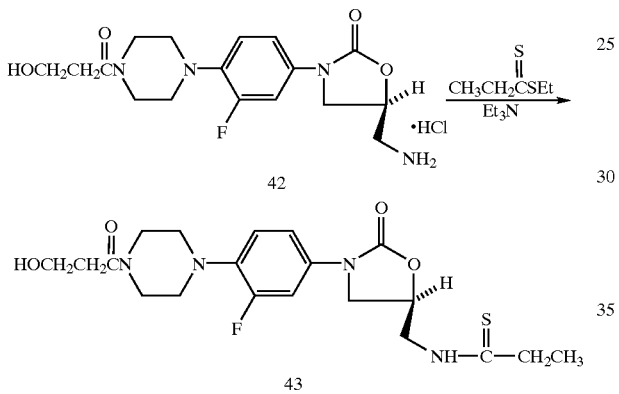

A stirred mixture of 42 (0.07 g, 0.19 mmol), $CH_2Cl_2$ (8 mL) and THF (8 mL) is treated with triethylamine (0.20 mL) and ethyl dithiopropionate (0.08 mL) and kept at ambient temperature (24° C.) for 24 hours, at 45° C. for 7.5 hours and at ambient temperature for 16 hours. It is then concentrated and the residue is chromatographed on silica gel with mixtures of MeOH—$CH_2Cl_2$ that contained 2–3.5% MeOH. The product (43) amounted to 0.057 g: HRMS (FAB) calcd for $C_{20}H_{28}FN_4O_4S$ (M+H$^+$) 439.1815, found 439.1812.

Example 14

Preparation of N-{[(5S)-3-(3-fluoro-4-{4-[(1-hydroxycyclopropyl)carbonyl]-1-piperazinyl}phenyl)-2-oxo-1,3-oxazolidin-5-yl]methyl}propanethioamide (44) (PNU-251110)

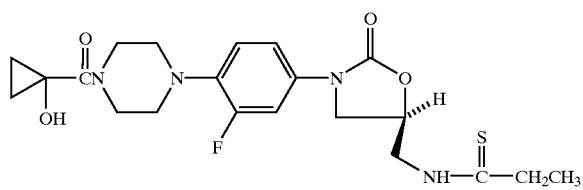

As described in Example 8 (Steps 4–6) 1-hydroxy-1-cyclopropanecarboxylic acid is coupled with 7 and the resulting amide is deprotected and allowed to react with ethyl dithiopropionate and triethylamine. The product is purified by silica gel chromatography with mixtures of MeOH—$CH_2Cl_2$ that contained 2–12% MeOH and by crystallization from MeOH—EtOAc to give 44: mp 185–186° C. (dec); MS(ES) m/z 451 (M+H$^+$), 473 (M+Na$^+$). Anal. calcd for $C_{21}H_{27}FN_4O_4S$: C, 55.99; H, 6.04; N, 12.44. Found: C, 55.78; H, 6.09; N, 12.18.

Example 15

Preparation of N-[((5S)-3-{3-fluoro-4-[4-(2-phenoxyacetyl)-1-piperazinyl]phenyl}-2-oxo-1,3-oxazolidin-5-yl)methyl]propanethioamide (47) PNU-251037)

Step 1

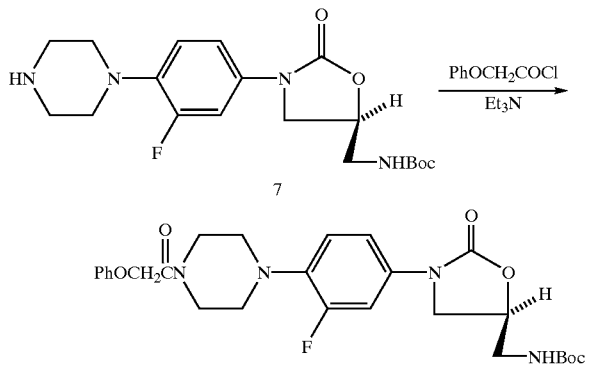

An ice cold, stirred solution of 7 (0.5 g, 1.26 mmol) and triethylamine (0.385 ml, 2.76 mmol) in $CH_2Cl_2$ (25 ml), under nitrogen, is treated dropwise with a solution of phenoxyacetyl chloride (0.35 ml, 2.52 mmol) in $CH_2Cl_2$ (3 ml) and kept in the ice bath for 2 hours and at ambient temperature for 30 minutes. It is diluted with $CH_2Cl_2$, washed with saturated $NaHCO_3$, water and brine, dried ($Na_2SO_4$) and concentrated. Crystallization of the residue from MeOH—EtOAc gave 0.53 g of 45: MS(ES) m/z 529 (M+H$^+$), 551 (M+Na$^+$).

Step 2

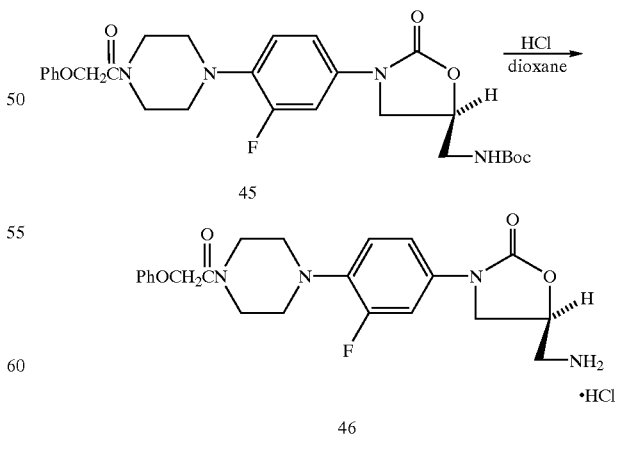

As described in Example 8 (Step 5) compound 45 is deprotected with hydrogen chloride in dioxane to give 46: MS(ES) m/z 429 (M+H$^+$).

Step 3

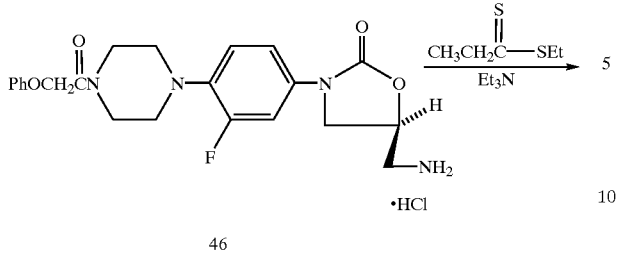

46

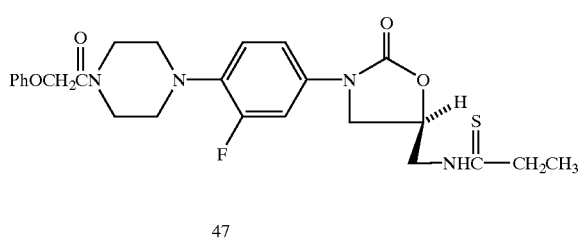

47

As described in Example 8 (Step 6) the amine hydrochloride (46) is allowed to react with ethyl dithiopropionate and triethylamine in $CH_2Cl_2$-THF. The product is chromatographed on silica gel with 2.5% MeOH—$CH_2Cl_2$ and crystallized from EtOAc to give 47: mp 171–172° C.; MS(ES) m/z 501 (M+H$^+$), 523 (M+Na$^+$). Anal. Calcd for $C_{25}H_{29}FN_4O_4S$: C,:59.98; H, 5.84; N, 11.19. Found: C, 59.59; H, 5.89; N, 11.03.

Example 16

Preparation of N-({(5S)-3-[3-fluoro-4-[4-((2S)-2,3-dihydroxypropanoyl)-1-piperazinyl]phenyl]-2-oxo-1,3-oxazolidin-5-yl}methyl)propanethioamide (48) (PNU-248440)

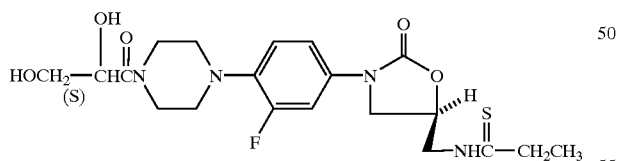

48

As described in Example 8 (Steps 4–6) L-glyceric acid, calcium salt dihydrate is coupled with 7 and the resulting amide is deprotected and allowed to react with ethyl dithiopropionate and triethylamine. The product is purified by silica gel chromatography with 7.5% MeOH—EtOAc to give 48: mp 142° C. (dec); MS(ES) m/z 455 (M+H$^+$), 477 (M+Na$^+$). Anal. Calcd for $C_{20}H_{27}FN_4O_5S$·0.3 EtOAc: C, 52.94; H, 6.15; N, 11.65, Found: C, 52.75; H, 6.02; N, 11.53.

Example 17

Preparation of N-({(5S)-3-[3-fluoro-4-[4-((2R)-2,3-dihydroxypropanoyl)-1-piperazinyl]phenyl]-2-oxo-1,3-oxazolidin-5-yl}methyl)propanethioamide (49) (PNU-248438)

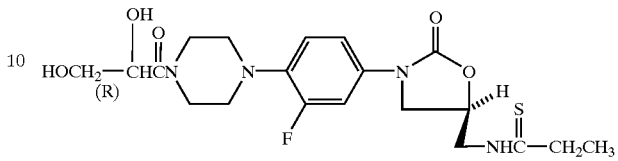

49

As described in Example 8 (Steps 4–6) D-glyceric acid, calcium salt dihydrate is coupled with 7 and the resulting amide is deprotected and allowed to react with ethyl dithiopropionate and triethylamine. The product is purified by silica gel chromatography with 7.5% MeOH—$CH_2Cl_2$ and crystallized from EtOAc-hexane to give 49: mp 132° C. (dec); MS(ES) m/z 455 (M+H$^+$), 477 (M+Na$^+$). Anal. Calcd for $C_{20}H_{27}FN_4O_5S$. 0.5 $H_2O$: C, 51.88; H, 6.09; N, 12.09; $H_2O$, 3.88. Found: C, 51.77; H, 6.09; N, 11.96; $H_2O$, 3.85.

Example 18

Preparation of N-{[(5S)-3-(3-fluoro-4-{4-[3-hydroxy-2-(hydroxymethyl)-2-mnethylpropanoyl]-1-piperazinyl}phenyl)-2-oxo-1,3-oxazolidin-5-yl]methyl}propanethioamide (50) (PNU-248437)

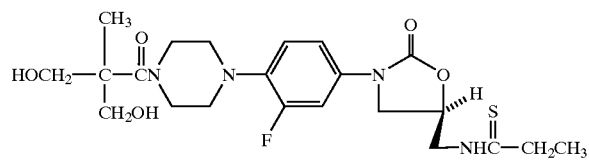

50

As described in Example 8 (Steps 4–6) 2,2-bis(hydroxymethyl)propionic acid is coupled with 7 and the resulting amide is deprotected and allowed to react with ethyl dithiopropionate and triethylamine. The product is purified by silica gel chromatography with 5% MeOH—$CH_2Cl_2$ and crystallized from MeOH—EtOAc-hexane to give 50: mp 202–203° C. (dec); MS(ES) m/z 483 (M+H+), 502 (M+Na$^+$). Anal. Calcd for $C_{22}H_{31}FN_4O_5S$: C, 54.76; H, 6.47; N, 11.61. Found: C, 54.38; H, 6.54; N, 11.43.

Example 19

Prepaxation of N-[((5S)-3-{3-fluoro-4-[4-((2S)-2-hydroxy-3-phenylpropanoyl)-1-piperazinyl]phenyl}-2-oxo-1,3-oxazolidin-5-yl)methyl]propanethioamide (51) (PNU-246967)

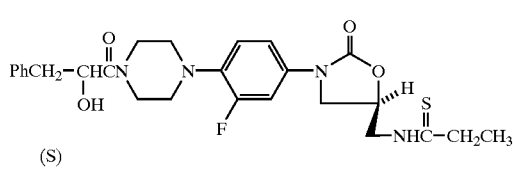

51

As described in Example 8 (Steps 4–6) L-3-phenyllacetic acid is coupled with 7 and the resulting amide is deprotected and allowed to react with ethyl dithiopropionate and triethylamine. The product is purified by silica gel chromatography with 2.5% MeOH—$CH_2Cl_2$ and crystallized from EtOAc-hexane to give 51: mp 174–175° C. Anal calcd for $C_{26}H_{31}FN_4O_4S$: C, 60.68; H, 6.07; N, 10.89. Found: C, 60.56; H, 6.17; N, 10.68.

Example 20

Preparation of N-[((5S)-3-{3-fluoro-4-[4-((2R)-2-hydroxy-3-phenylpropanoyl)-1-piperazinyl]phenyl}-2-oxo-1,3-oxazolidin-5-yl) methyl] propanethioamide (52) (PNU-246966)

52

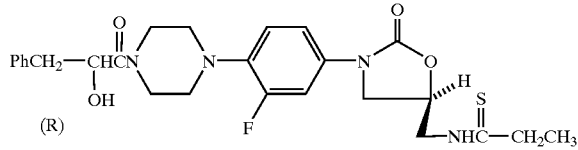

As described in Example 8 (Steps 4–6) D-3-phenyllactic acid is coupled with 7 and the resulting amide is deprotected and allowed to react with ethyl dithiopropionate and triethylamine. The product is purified by silica gel chromatography with 2.5% MeOH—$CH_2Cl_2$ and crystallized from EtOAc-hexane to give 52: mp 128–130° C. (dec). Anal. Calcd for $C_{26}H_{31}FN_4O_4S$: C, 60.68; H, 6.07; N, 10.98. Found: C, 60.50; H, 6.17; N, 10.80.

Example 21

Preparation of N-[((5S)-3-{3-fluoro-4-[4-((2R)-2-hydroxy-2-phenylacetyl)-1-piperazinyl]phenyl}-2-oxo-1,3-oxazolidin-5-yl)methyl]propanethioamide (53) (PNU-245689)

53

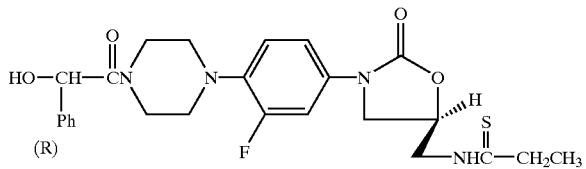

As described. in Example 8 (Steps 4–6) (R)-(−)-mandelic acid is coupled with 7 and the resulting amide is deprotected and allowed to react with ethyl dithiopropionate and triethylamine. The product is purified by silica gel chromatography with mixtures of MeOH—$CH_2Cl_2$ containing 2–3.5% MeOH to give 53: HRMS (FAB) calcd for $C_{25}H_{30}FN_4O_4S$ (M+H$^+$) 501.1971, found: 501.1980.

Example 22

Preparation of N-[((5S)-3-{3-fluoro-4-[4-((2S)-2-acetoxy-2-phenylacetyl)-1-piperazinyl]phenyl}-2-oxo-1,3-oxazolidin-5-yl)methyl]propanethioamide (54) (PNU-245878)

54

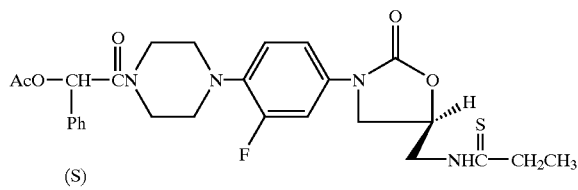

As described in Example 8 (Steps 4–6) (S)-(+)-O-acetylmandelic acid is coupled with 7 and the resulting amide is deprotected and allowed to react with ethyl dithiopropionate and triethylamine. The product is purified by silica gel chromatography with 2% MeOH—$CH_2Cl_2$ to give 54: HRMS (FAB) calcd for $C_{27}H_{32}FN_4O_5S$ (M+H$^+$) 543.2077, found: 543.2063.

What is claimed is:

1. A compound of formula I

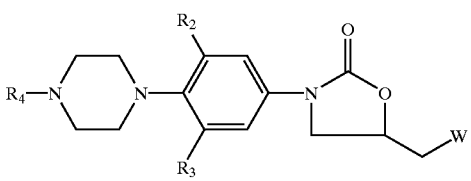

I or a pharmaceutically acceptable salt thereof wherein:

W is NHC(=S)$R_1$, $R^1$ is
(a) H,
(b) $NH_2$,
(c) $NHC_{1-4}$ alkyl,
(d) $C_{2-4}$ alkenyl,
(e) $OC_{1-4}$ alkyl,
(f) $SC_{1-4}$ alkyl,
(g) $(CH_2)_n$-$C_{3-6}$ cycloalkyl, or
(h) $C_{1-4}$ alkyl, optionally substituted with 1–3 F, 1–2 Cl or CN;

$R_2$ and $R_3$ are independently H, F, Cl or $C_{1-2}$ alkyl;

$R_4$ is
(a) —C(=O)—$CH_2S(O)_n$—$CH_3$,
(b) —C(=S)$C_{1-4}$ alkyl,
(c) —C(=O)—$(CH_2)_m$—C(=O)—$CH_3$,
(d) —C(=O)—$CH_2$—O—$R_{10}$, or
(e) —CN;

$R_{10}$ is —$CO_2$—$(CH_2)_2$—$OCH_3$, or —C(=O)—$NHC_{1-4}$alkyl;

n is 0, 1 or 2; and m is 0 or 1.

2. A compound of formula I according to claim 1 which is an optical configuration of formula Ia,

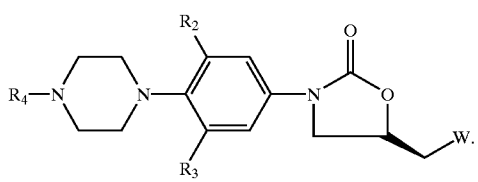

Ia

3. A compound of formula I according to claim 1 wherein $R_1$ is $C_{1-4}$ alkyl.

4. A compound of formula I according to claim 1 wherein $R_1$ is ethyl.

5. A compound of formula I according to claim 1 wherein $R_2$ and $R_3$ are independently H or F.

6. A compound of formula I according to claim 1 wherein $R_2$ is H, $R_3$ is F.

7. A compound of claim 1 which is
(a) N{[(5S)-3-(3-fluoro-4-{4-[2-(methylsulfinyl)acetyl]-1-piperazinyl}phenyl)-2-oxo-1,3-oxazolidin-5-yl]methyl}propanethioamide,
(b) N-{[(5S)-3-(3-fluoro-4-{4-[2-(methylsulfanyl)acetyl]-1-piperazinyl}phenyl)-2-oxo-1,3-oxazolidin-5-yl]methyl}propanethioamide, or (c) N-{[(5S)-3-(3-fluoro-4-{4-[2-(methylsulfonyl) acetyl]-1-piperazinyl}phenyl]-2-oxo-1,3-oxazolidin-5-yl]methyl}propanethioamide.

8. A compound of claim 1 which is N-({(5S)-3-[4-(4-cyano-1-piperazinyl)-3-fluorophenyl]-2-oxo-1,3-oxazolidin-5-yl}methyl)propanethioamide.

9. A compound of claim 1 which is
   (a) N-({(5S)-3-(3-fluoro-4-{4-[2-(methylaminocarbonyloxy)acetyl]-1-piperazinyl}phenyl)-2-oxo-1,3-oxazolidin-5-yl}methyl)propanethioamide,
   (b) N-({(5S)-3-(3-fluoro-4-{4-[2-[(2-methoxyethoxy)carbonyloxy]acetyl]-1-piperazinyl}phenyl)-2-oxo-1,3-oxazolidin-5-yl}methyl)propanethioamide or
   (c) N-({(5S)-3-[3-fluoro-4-(4-acetoacetyl-1-piperazinyl)phenyl]-2-oxo-1,3-oxazolidin-5-yl}methyl)propanethioamide.

10. A compound of claim 1 which is N-({(5S)-3-[3-fluoro-4-(4-pyruvoyl-1-piperazinyl) phenyl]-2-oxo-1,3-oxazolidin-5-yl}methyl)propanethioamide.

11. A compound of claim 1 which is a structure Ib

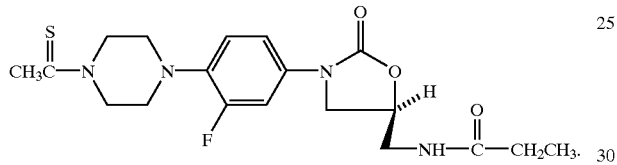

Ib

12. A method for treating microbial infections in mammals comprising administration of an effective amount of a compound of claim 1 to said mammal.

13. The method of claim 12 wherein said compound is administered to the mammal orally, parenterally, transdermally, or topically in a pharmaceutical composition.

14. The method of claim 12 wherein said compound is administered in an amount of from about 0.1 to about 100 mg/kg of body weight/day.

15. The method of claim 12 wherein said compound is administered in an amount of from about 1 to about 50 mg/kg of body weight/day.

16. The method of claim 12 wherein the infection is skin infection.

17. The method of claim 12 wherein the infection is eye infection.

18. A pharmaceutical composition comprising a compound of claim 1 and a pharmaceutically acceptable carrier.

19. N-[((5S)-3-{3-fluoro-4-[4-((2S)-2-acetoxy-2-phenylacetyl)-1-piperazinyl]phenyl}1,3-oxazolidin-5-yl)methyl]propanethioamide.

* * * * *